United States Patent [19]

Pommez

[11] Patent Number: 4,522,874
[45] Date of Patent: Jun. 11, 1985

[54] ABSORBENT ARTICLE STRUCTURE AND ABSORBENT ARTICLE

[76] Inventor: Philippe J. Pommez, Cassio da Costa Vidigal St. - 27 - 4th Floor, Sao Paulo, Brazil

[21] Appl. No.: 613,492

[22] Filed: May 24, 1984

[30] Foreign Application Priority Data

Jun. 29, 1983 [BR] Brazil .................................. 8303466

[51] Int. Cl.³ ................................................ C08K 5/01
[52] U.S. Cl. ..................................... 428/284; 428/351; 428/354; 428/355; 428/356; 604/389; 604/390
[58] Field of Search ................. 604/389, 390; 428/284, 428/286, 290, 913, 351, 354, 355, 356

[56] References Cited

U.S. PATENT DOCUMENTS

| | | | |
|---|---|---|---|
| 2,649,858 | 8/1953 | Le Bolt | 604/389 X |
| 2,834,347 | 5/1958 | Connally | 604/389 |
| 3,049,228 | 8/1962 | Burnett | 604/389 X |
| 3,162,610 | 12/1964 | Samour | 428/356 X |
| 4,037,016 | 7/1977 | Habeck et al. | 428/355 X |
| 4,112,177 | 9/1978 | Salditt et al. | 428/355 X |
| 4,240,860 | 12/1980 | Pole et al. | 428/356 X |
| 4,288,480 | 9/1981 | Grzywinski et al. | 428/355 X |

*Primary Examiner*—George F. Lesmes
*Assistant Examiner*—Nancy A. B. Swisher

[57] ABSTRACT

An absorbent article structure is provided comprising a permeable, internal layer (10), an intermediate absorbent layer (20) and a liquid-impervious, outer layer (30). Outer layer (30) comprises an inherently-porous paper length (32) impregnated with a selective adhesive forming a liquid-impervious and air-permeable coat (34), which only adheres to itself. A disposable diaper (50) can be manufactured with the structure, being entirely degradable and eliminating the "greenhouse" effect of traditional diapers having an outer plastic layer. The self-sticking properties of the coat (34) eliminate the need for tapes and tabs on the diaper.

6 Claims, 2 Drawing Figures

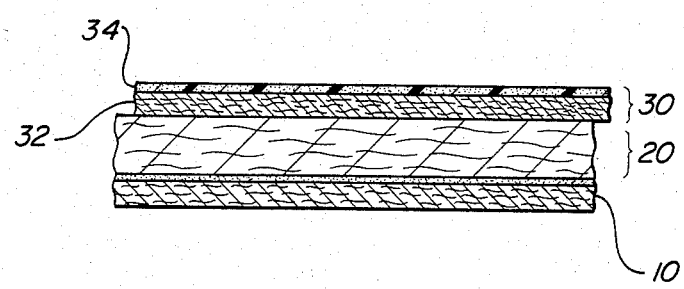
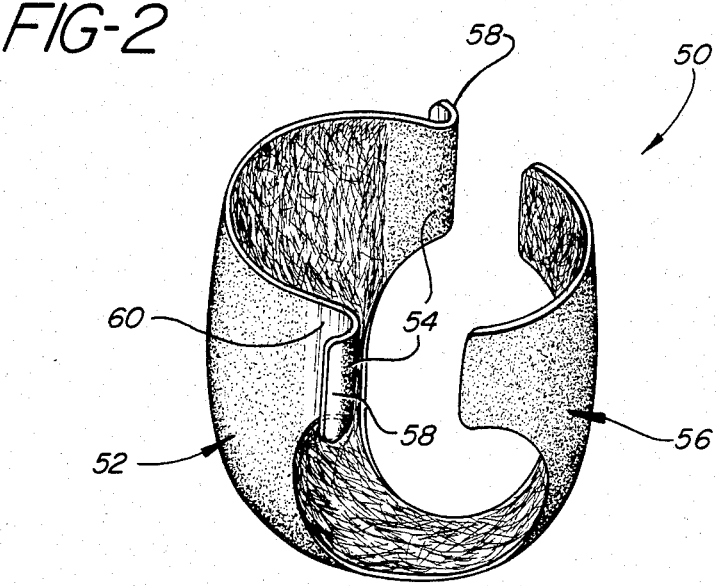

ABSORBENT ARTICLE STRUCTURE AND ABSORBENT ARTICLE

BACKGROUND OF THE INVENTION

The present invention refers generally to structures for absorbent articles and to absorbent articles as, for example, disposable napkins and diapers and, more specifically, to an absorbent article structure and to articles manufactured with such structure, wherein the outer, impervious layer of the structure and articles is made of an inherently-porous paper substrate impregnated with a selective adhesive which only adheres to itself, so that the structure and the articles become impervious to liquids and permeable to air, the articles — as for example disposable diapers — eliminating the use of safety pins, buttons, tapes and tabs for their closure on the wearer's body.

The current technique in the manufacture of absorbent structures — as, for example, diapers or surgical sheets — is based on the use of three basic layers of material: an internal, permeable layer, usually made of a non-woven cellulosic fabric or of a highly-porous and absorbent paper; an intermediate layer, of a highly absorbent material, usually made of a loosely-compacted fibrous material; and an outer layer, impervious to liquids, usually made of a plastic material.

Such structures have been known for a long time, and impervious outer layers, made, for example, of a thoroughly impervious material — as rubber and several types of plastics — with the layers being able to be an integral part of the structure or detachable from other layers, are current in the patent literature since the beginning of this century.

It so happens that all such structures, especially when shaped as diapers, produce a so-called "greenhouse" effect, causing great discomfort to the wearer. Attempts to overcome the problems caused by the greenhouse effect, with the provision of microscopic perforations and tubes with capillary action, preventing the migration of liquid and enabling breathing of the diaper, are disclosed in recent but the difficulties of accurate manufacture of such structures with the extremely high rates desired in the manufacture of absorbent articles produce certain disadvantages in such types of structure.

The widespread use of plastics as the impervious outer layer contributes substantially to the problem known as the "greenhouse" effect. The use of plasticized paper, as in U.S. Pat. No. 2,627,858, (1950), does not contribute to a solution, since the impregnation of paper with polystyrene on its surface renders the outer layer impervious both to liquid and air.

In the absorbent articles where a portion of the articles should be adhered to another portion for the formation of a garment, as in diapers, a countless number of fastening devices has been proposed in the prior art, from the traditional safety pins, common or pressure buttons, hooks, tapes capable of forming knots, with the fastening devices most widespread now being adhesive tapes. Usually, the adhesive tapes are attached to or fastened on the impervious outer layer of the diaper, having an adhesive surface which remains folded over and protected until the moment of its use. In some cases, as in U.S. Pat. No. 2,649,858, (1951), U.S. Pat. No. 3,620,217, (1970), U.S. Pat. No. 3,901,237, (1974) or in U.S. Pat. No. 2,290,110, (1941), adhesive areas are provided in certain zones of the diaper, which remain duly protected until the moment of use. In other cases, as in U.S. Pat. No. 4,055,181, (1976), and U.S. Pat. No. 4,034,752, (1976), the tapes are "built in" the diaper and do not protrude outwardly. Some of the above-mentioned patents enable, in one way or another, the adjustment or reutilization of the diaper, and the fastening device can be opened and closed again.

The drawback of the fastening devices used until now lies in the fact that their manufacture and installation in the diapers are laborious and expensive steps which complicate the manufacturing process, which process should be necessarily fast and simple in order that a disposable diaper reaches the market with a reasonable cost.

One advantage of the present invention is the provision of a structure in which the outer layer is impervious to liquid and permeable to air, eliminating the "greenhouse" effect on articles made with this structure. Also the need for separate fastening means is eliminated. The closure of the present invention can be opened and resealed repeatedly. Furthermore, the entire product can be made without the use of non-breathable plastic materials.

These and other objects of the invention can be better understood by reading the following detailed description and the accompanying drawings.

BRIEF DESCRIPTION OF THE DRAWINGS

FIG. 1 is a schematic, cross-sectional view of the structure of the present invention; and FIG. 2 is a perspective view of an article made with the structure of the invention, in this case a diaper.

SUMMARY OF THE INVENTION

The present invention provides an absorbent article structure which has a liquid-permeable facing, an absorbent intermediate layer and a liquid-impervious outer layer. The liquid-impervious outer layer comprises a porous paper-like substrate having one surface thereof coated with a selective adhesive which adheres only to itself. The adhesive is comprised of an aqueous ammoniacal emulsion having about 60 percent solids and about 0.003 percent ammonia. The solids are about 85 parts by weight poly-cis-isoprene and and about 15 parts by weight vinyl acetate and n-butyl acrylate.

DETAILED DESCRIPTION OF THE INVENTION

Referring to the drawings and, more specifically, FIG. 1, we can see that the absorbent structure of the present invention comprises basically a liquid-permeable, internal layer 10, made of a non-woven fibrous material, of a highly-porous paper, or any other known material, in contact with an intermediate layer 20, of an absorbent material, usually comprised of loosely-compacted cellulosic short-fiber material. Layer 10 can be adhered to layer 20 or not, by means of an adhesive or any other suitable means.

The present invention provides a liquid-impervious, outer layer 30, in contact with intermediate surface 20. According to the invention, the structure's outer layer 30, comprises an inherently-porous paper length 32, directly engaging the surface of intermediate layer 20. The outer surface of the structure's paper length 32, is impregnated with a coat 34, of an adhesive formulation preferably comprised of an aqueous ammoniacal emulsion at about 60 percent solids and about 0.003 percent ammonia.

The most preferred solids content in the emulsion for use as an impregnator of layer 34 includes about 85 percent poly-cis-isoprene, originating from natural rubber, and about 15 percent of a mixture of polymers of vinyl acetate and n-butyl acrylate.

The inherently-porous paper length 32, can be comprised of any other type of paper or of woven or non-woven fabric that will accept impregnation with the emulsion of the invention.

The preferred impregnating emulsion of the present invention can be described as a selective self-sticking glue, which only adheres to itself and has the following properties:

(a) it is entirely impervious to liquids, thereby providing paper length 32, with the necessary and sufficient properties to function as an impervious outer layer in an absorbent article;

(b) it is air permeable, reducing or eliminating the greenhouse effect noted in articles where the impervious outer layer is made of plastic. In one of the samples tested, outer layer 30, of the structure of the invention showed air permeability of about 1,600 to about 2,000 seconds for every 100 ml of air;

(c) paper length 32 and the impregnate of coat 34 are much more easily degradable than prior art polymer plastic materials, contributing to reduction of pollution after articles made with the structure of the invention are disposed of;

(d) the adhesive resistance of layer 34, when stuck to itself, to shear forces, i.e., to a force of 1 kg, exceeds 20 hours, which compares favorably against the resistance of adhesives conventionally used in diaper tabs;

(e) the repeatability of opening the closure in accordance with the invention and readhering the same parts that were released enable an article manufactured with the structure of the invention to be adjustable on the wearer's body or allows it to be used again. The force for peeling off an impregnated surface from another ranges from about 0.031 kg.cm/cm to about 0.046 kg.cm/cm, and the adhesion and separation can be made over 50 times. Usually, in those adhesives commonly used in prior art, directly fastened to plastic polymers, such forces cannot be measured, since plastic is torn out when one tries to unstick the layers. Most adhesives enabling reuse require special surfaces which make the final product more expensive or render useless the area receiving for the first time the adhesive, which impairs the adjustment of the articles.

The structure of the present invention enables the fast manufacture of articles, as disposable diapers, in large numbers and at a low cost. An embodiment of a diaper that can be built with the structure of the invention is shown in FIG. 2. Diaper 50 has an impervious, outer layer 52, made of a paper length impregnated with the adhesive in accordance with what was stated above. Ears, or projections 54, of the back portion of the diaper, are also impregnated with the adhesive of the invention from inside, which enables its selective adhesion in any position on the outer surface, also impregnated, of the front portion 56, of the diaper. The qualities of the invention's adhesive enable the fastening and refastening of ear 54 until a perfect fit on the wearer's body is obtained, or permits the diaper to be removed and used again later. Small extensions of ends 58 of ears 54 can be left with no impregnation, facilitating the removal of the diaper, when desired. Diapers made, as described, eliminate entirely the need for fastening devices, as tabs or tapes in current use. Area 60 of the outer surface of the outer layer of the diaper can be impregnated or not with the adhesive of the invention, and this will not impair the final use of the diaper, since usually it will overlie the front portion 56 of the diaper.

It is obvious to those skilled in the art that a number of alterations and modifications can be introduced in the present invention without departing from the spirit and scope of the invention as claimed in the claims appended.

I claim:

1. An absorbent article structure, comprising a liquid-permeable, internal layer (10), an absorbent, intermediate layer (20) and a liquid-impervious, outer layer (30), wherein the liquid-impervious layer (30) comprises an inherently-porous paper length (32) the outer surface of which is impregnated with a coat (34) of a selective adhesive which only adheres to itself, the adhesive coat (34) being comprised of an aqueous ammoniacal emulsion having about 60 percent solids and about 0.003 percent ammonia, the solids content in the emulsion comprising about 85 percent poly-cis-isoprene and about 15 percent of a mixture of polymers of vinyl acetate and n-butyl acrylate.

2. A structure in accordance with claim 1 wherein the inherently-porous paper length (32) is a non-woven fibrous fabric.

3. An article made with the structure in accordance with claim 1 or 2 wherein a certain area (54) of the internal surface of the paper length is free from the internal and intermediate layers (10 and 20) and in that it is impregnated with the adhesive of claim 1.

4. An article in accordance with claim 3 wherein the impregnated area (54) of the internal surface which is free from the internal and intermediate layers (10 and 20) is provided on projections, or ears, of the article.

5. An article in accordance with claim 4 wherein the ends (58) of the areas (54) are free from adhesive impregnation.

6. An article in accordance with claim 3 wherein the area (54) is an area formed in an opening of the internal and intermediate layers (10 and 20).

* * * * *